United States Patent [19]

Haindl

[11] Patent Number: 5,679,442
[45] Date of Patent: Oct. 21, 1997

[54] SHELF-LIFE INDICATOR FOR REPEATEDLY STERILIZABLE PLASTIC PRODUCTS

[76] Inventor: Hans Haindl, Hauptstrasse 39, D-30974 Wennigsen, Germany

[21] Appl. No.: 507,479

[22] PCT Filed: Mar. 31, 1994

[86] PCT No.: PCT/DE94/00374

§ 371 Date: Aug. 28, 1995

§ 102(e) Date: Aug. 28, 1995

[87] PCT Pub. No.: WO94/23763

PCT Pub. Date: Oct. 27, 1994

[30] Foreign Application Priority Data

Apr. 10, 1993 [DE] Germany .......... 43 11 846.1

[51] Int. Cl.$^6$ .......................................... B32B 3/00
[52] U.S. Cl. .......................... 428/195; 428/199; 428/204; 428/207; 428/411.1; 428/419; 428/473.5; 428/474.4; 428/480; 428/500; 428/913
[58] Field of Search .................... 428/195, 204, 428/211, 411.1, 423.1, 474.4, 488.4, 688, 913, 914, 199, 207, 419, 473.5, 480, 500

[56] References Cited

U.S. PATENT DOCUMENTS

| | | |
|---|---|---|
| 3,932,134 | 1/1976 | Fang et al. . |
| 3,996,007 | 12/1976 | Fang et al. . |
| 4,038,873 | 8/1977 | Kimmel . |
| 4,311,479 | 1/1982 | Fenn et al. . |
| 4,533,640 | 8/1985 | Shafer . |
| 4,737,463 | 4/1988 | Bhattacharjee et al. . |
| 4,795,714 | 1/1989 | Shafer . |

FOREIGN PATENT DOCUMENTS

| | | |
|---|---|---|
| 0 069 037 | 1/1983 | European Pat. Off. . |
| 0 581 400 | 2/1994 | European Pat. Off. . |
| 28 41 749 | 4/1979 | Germany . |
| 29 29 582 | 2/1981 | Germany . |
| 31 03 936 | 8/1982 | Germany . |
| 31 26 275 | 1/1983 | Germany . |
| 4-364174(A) | 12/1992 | Japan . |

*Primary Examiner*—William Krynski
*Attorney, Agent, or Firm*—Burns, Doane, Swecker & Mathis, L.L.P.

[57] ABSTRACT

Described is a shelf-life indicator for repeatedly sterilizable plastic products. The shelf-life indicator consists of a polymer incorporating heterogeneously distributed pigments. These pigments are further distributed, under the repeated action of heat, by diffusion so that a change in color takes place which indicates the end of the useful life of the plastic product. The shelf-life indicator can be combined with the plastic product.

19 Claims, 1 Drawing Sheet

[5,679,442]

SHELF-LIFE INDICATOR FOR REPEATEDLY STERILIZABLE PLASTIC PRODUCTS

FIELD OF THE INVENTION

The invention relates to a shelf-life indicator for repeatedly sterilizable plastic products.

BACKGROUND OF THE INVENTION AND BRIEF DESCRIPTION OF THE PRIOR ART

In the medical field, in order to contribute to waste reduction, more and more products are used that are only partially disposable and the other parts can be reused. In general, these reusable parts are made of plastic products sterilizable under the action of steam. A problem met by these products is that the shelf-life of the plastic products sterilizable under the action of steam is limited. Thus, the hazard exists that after repeated sterilization they break while being used. The consequences of this could be detrimental under certain circumstances, if broken parts fall in the region of a wound or if an important step of an operation cannot be completed by the surgeon because the instrument is broken.

In general, products of this kind are made so that they can undergo 100 sterilizations without being damaged. It is obvious to find an indicator that signals the user that the product is exhausted and should not be used any more.

However, this problem is not easy to solve. Before the resterilization, the products are in general treated in automatic washing machines with partially very abrasive cleaning products. In each case, the reaction of an indicator set on the outer surface would depend more on the cleaning product than on the sterilization itself. This is why trying to set color indicators on the outer surface has been unsuccessful until now.

According to DE 31 26 275 A1, it is known how to provide medical devices with indicators for sterilization processes. The indicator used is a pigment that changes its color under the influence of the sterilization process used and so indicates that the sterilization has occurred. Such indicators are appropriate only for non-reusable products. Besides, in ZIP 4-364174 A, Patents Abstracts of Japan, See. C, Vol. 17, No. 232 (C-1056), an indicator means for sterilization processes of medical devices is described and this indicator means is appropriate for steam sterilization as well as for sterilization with ethylene oxide.

Moreover, a sterilizable packing for items used in the medical field is known from DE 29 29 582 A1. In its closed internal part, the packing has a humidity indicator in the form of an externally visible color that changes constantly under the penetration of humidity.

Finally, it is known from DE 31 03 936 A1 how to color polymer materials by converting a colorant from a solution or from the gaseous phase into the transparent polymer material by diffusion.

DESCRIPTION OF THE INVENTION AND PREFERRED EMBODIMENTS

The invention is based on the problem of specifying an indicator that signals that the sterilizable material should not be used any more.

This problem is solved by a shelf-life indicator with the characteristics described infra and in the Figures. The action of the invention, which consists of the diffusion and/or of the modification of the pigments put in the polymer under the repeated action of heat, is based on the following behavior. The pigments diffuse themselves between the molecules in the polymer according to the temperature. The migration of the molecules occurs here in three dimensions, therefore, the original concentration at the location where it had been incorporated decreases. In addition, in the course of the repeated action of heat on the polymer, reactive disintegration products result which engage and so modify the pigments. Under the term modification, any kind of modification and even destruction is understood. The concentration of the pigment decreases in this way too.

The portions that the diffusion and the destruction of the pigments have on their concentration at the original incorporation location depend on the kinds of the pigments and polymer. Since both effects go in the same direction, the knowledge of their portions is of subordinate importance in practice. In each case, the result of each steam sterilization is a further slight diffusion of the pigments and the modification of individual pigments, so that the pigmentation becomes more faded with each sterilization, at first imperceptibly, later more noticeably. With the suitable balancing between the polymer and the pigment, it can be achieved that the pigmentation disappears after about 100 sterilizations.

Since the pigments are incorporated into the polymer and always penetrate deeper into it though further diffusion, they cannot be removed or damaged by superficial cleaning processes.

With regard to the arrangement of the pigments in the polymer, several possibilities exist. Thus, the pigments can be at first incorporated evenly on or close to the visible surface. Then, the color intensity decreases in the course of the sterilizations, since the pigments constantly penetrate to deeper layers or are modified, so that their concentration decreases on the upper surface. In this case, it is difficult to estimate at which color intensity the sterilizable product should not be used any more without comparison. Further, the pigments can be initially incorporated with an irregular distribution on or close to the visible surface. It is particularly suitable for this to incorporate the pigments in the form of a writing or a geometrical figure. After each sterilization the clarity of the contours of this kind of pigmentation will lessen until all the originally discrete surfaces have eventually merged. This design permits a significantly better definition of the time when the sterilizable product should not be used any more.

An example of such a sign is to write "reusable". Then, the pigments are present at first in a high concentration at prescribed locations and they are not present at the other locations. The sharp contours of the letters exist at first, which become less and less sharp with the increasing of diffusion and finally merge together, so that the word is then illegible.

In addition, the polymer can have properties of light scattering and/or of light absorption. Thanks to this measure, the visibility of the pigments deep in the polymer is hindered, so that the diminution of the color intensity accelerates with each sterilization.

Another choice is to incorporate the pigments at a distance from the visible surface, if the polymer is optically clear. If the pigment distribution is initially regular, it will result in a noticeable fading, essentially due to pigment modification, while if the pigment distribution is at first irregular, the originally sharp contours fade through pigment diffusion.

It is preferable to use polymers of the group of the polyamide, polyester, polyacetals, polysulfone and polyimide as carrying material for the pigments. These polymers keep their form at the usual sterilization temperatures and they allow the pigments to have a diffusion velocity at which the rate of the fading or the progression of the pigments can be used as a criterion for the end of the useful life of the reusable plastic product. A development of this provides that filling materials are added to the polymer. A material adequate to be filling material is the talcum (silicium oxide). It has been shown that thanks to it there can be a clear improvement of the diffusion behavior of the polymers that permit only a little diffusion when they are not filled, and so the filling materials, in another respect, allow the balancing of the fading of the pigments at each sterilization with the favorable number of sterilization cycles.

The azo dyes, e.g. the azo dye C.1. Disperse Yellow, are suitable as pigments. For typical sterilization temperatures, the azo dyes are temperature stable and they can diffuse inside the polymer. The respective properties of the polymers and of the azo dyes are balanced with one another such that their combination allows a practical realization of the shelf-life indicator.

Dyes used as pigments and that are especially advantageous are the ones that can change from one color to another through the repeated action of heat. The color change allows a particularly clear indication of the end of the useful life of the reusable plastic products. This effect is also based on the influence of the reactive disintegration products that appear in the course of the repeated action of heat on the polymer, especially in the case of polyacetals, which engage and then modify the pigments. But in this case, the modification does not result in the destruction of the pigments, but in a color modification or change.

For a particularly favorable embodiment it is possible to use the fact that the pigments diffuse with different speeds in different plastic products. Then, for instance thanks to a double-layer structure with a difficult diffusing plastic product on the outer surface and an easy diffusing plastic product for the inner layer, one can accelerate the transfer of the pigments to the inner part. This leads to a clear color change, since the pigment does not diffuse parallel to the outer surface but into the inner part, which is advantageous.

In the case of a multi-layer structure the polymer layers can be stuck together without adhesive, for instance with ultrasonic welding, friction welding, high frequency welding or thermal contact welding. Thus, it is possible to achieve a direct transfer from one layer to another without having a disruptive intermediate layer.

It is advantageous to incorporate the pigments through intermolecular diffusion in the polymer after having brought them onto the upper surface of the polymer. Thus, the pigments are at first pressed from the surface into the polymer by means of a typical pressure process and eventually they reach into a deeper region through diffusion thanks to the action of temperature, so that they are protected from wearing away on the outer surface. Thus, a high color density in the polymer can be achieved for high temperatures. Tampon pressure, strainer pressure, offset pressure or ink stream pressure are suitable pressure processes.

Double-component injection molding is another possibility for incorporating the pigments into the polymer. In this case intermolecular diffusion is no longer necessary to penetrate the pigments deeper into the polymer.

Concerning the bond of the shelf-life indicator with the reusable product, the following advantageous possibilities exist. The shelf-life indicator can be a constructive part of the product, in that parts of the product are made of the polymers used to carry the pigments. Another possibility is to set the indicator as a nondetachable and heat-resisting adhesive label on the product.

EXAMPLE

One exemplary embodiment of the invention is described in more detail in the following. The drawings show:

Figure 1:
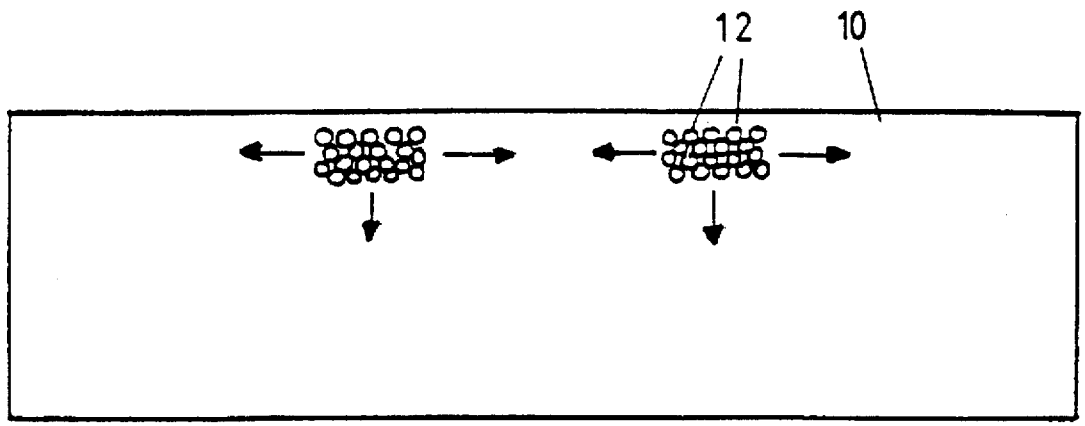
FIG. 1 a schematic cross section through a shelf-life indicator when it is new, and FIG. 2 a schematic cross section through a shelf-life indicator when used.
Figure 2:
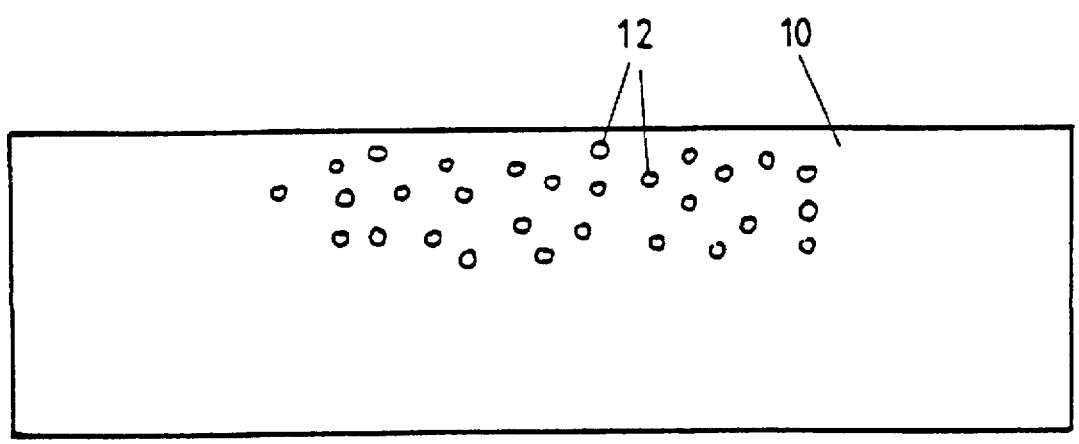

The FIGS. 1 and 2 show a cross-section through a shelf-life indicator. This consists of the polymer 10 that serves as a carrier and pigments 12. Only the outer delimitations of the polymer are represented while the pigments are drawn as round bodies. The representation does not give the real size ratio of the pigments to the polymer, but rather 8 it is a purely schematic drawing.

When it is new, according to FIG. 1, the pigments 12 are arranged in a ring close to the outer surface of the polymer 10. During each sterilization the pigments 12 diffuse a little further, which is represented by arrows. The migration of the pigments 12 occurs then in a three dimensional direction. In addition, some pigments are modified or destroyed.

After a number of sterilization processes, after which the end of the useful life of the reusable product is reached, there is a certain distribution of the pigments 12 in the polymer 10, as it is represented in FIG. 2. Then, the pigments are diffused and their number has decreased. The originally sharply defined regions of the ring which were covered by the pigments 12 have disappeared. Particularly, the pigments that have migrated from different positions to the middle of the ring are gathered, so that the originally free inner space appears now to be colored too. The user can use this as a clear criterion to determine that the end of the useful life has been reached and that the product should not be used any more.

I claim:

1. Shelf-life indicator, which is attached to or is capable of being attached to a plastic product that is to be subjected to repeated heat sterilizations, consisting of a polymer containing at least one pigment or azo dye which pigment or azo dye diffuses and/or becomes modified in the polymer after said polymer is subjected to repeated heat sterilizations, and wherein such diffusion and/or modification of said pigment or azo dye contained in the polymer provides a means of visually assessing the end of the useful shelf-life of said plastic product.

2. Shelf-life indicator as in claim 1, comprising azo dye or pigment that are initially incorporated therein such that is distribution is even on or close to a visible outer surface.

3. Shelf-life indicator as in claim 1, comprising azo dye or pigment that is initially incorporated therein such that their distribution is irregular on or close to a visible outer surface.

4. Shelf-life indicator as in claim 1, wherein the azo dye or pigment is initially incorporated such that it forms a word and/or a geometric figure on or close to a visible outer surface.

5. Shelf-life indicator as in claim 1, wherein the polymer scatters light or absorbs light.

6. Shelf-life indicator as in claim 1, wherein the azo dye or pigment is incorporated at a distance from a visible outer surface and wherein the polymer is transparent.

7. Shelf-life indicator as in claim 1, wherein the polymer is selected from the group consisting of polyamide, polyester, polyacetal, polysulfone and polyimide.

8. Shelf-life indicator as in claim 1, wherein the polymer comprises filler materials.

9. Shelf-life indicator as in claim 1, wherein azo dyes comprise said dye.

10. Shelf-life indicator as in claim 1, wherein said azo dye comprises a dye that exhibits a color change when subjected to repeated heat sterilizations.

11. Shelf-life indicator as in claim 1, wherein the polymer is comprised of two layers, whereby the azo dye or pigment diffuses in one layer at a different rate than in the other.

12. Shelf-life indicator as in claim 11, wherein both polymer layers are bound together by means other than an adhesive.

13. The shelf-life indicator of claim 12, wherein said polymer layers are bound together using a process selected from the group consisting ultrasonic welding, friction welding, high frequency welding and thermal contact welding.

14. Shelf-life indicator as in claim 1, wherein the pigment or azo dye is incorporated into the polymer by diffusion by applying the dye or pigment to an outer surface of the polymer.

15. Shelf-life indicator as in claim 1, wherein said azo dye or pigment is applied to the outer surface of said polymer by tampon pressure, strainer pressure, offset pressure or ink stream pressure.

16. Shelf-life indicator as in claim 1, wherein the azo dye on pigment is incorporated into the polymer via double-component injection molding.

17. Shelf-life indicator as in claim 1, wherein the indicator is an adhesive label, wherein said label is capable of being non-detachably adhered to the product when it is subjected to heat.

18. The shelf-life indicator as set forth in claim 1, wherein said shelf-life indicator constitutes part of the structure of a polymeric product.

19. Process for using a shelf-life indicator according to claim 1 for assaying the useful life of a plastic product which is subjected to repeated heating operations comprising subjecting a polymeric product containing the shelf-life indicator to repeated heating processes, and assessing the useful shelf-life of said product by visually detecting the degree of diffusion or modification of the pigments which are contained in said shelf-life indicator.

* * * * *